(12) United States Patent
Tai

(10) Patent No.: US 9,419,202 B2
(45) Date of Patent: Aug. 16, 2016

(54) ULTRASOUND TRANSDUCER AND METHOD FOR MANUFACTURING AN ULTRASOUND TRANSDUCER

(71) Applicant: General Electric Company, Schenectady, NY (US)

(72) Inventor: Alan Chi-Chung Tai, Phoenix, AZ (US)

(73) Assignee: General Electric Company, Schenectady, NY (US)

( * ) Notice: Subject to any disclaimer, the term of this patent is extended or adjusted under 35 U.S.C. 154(b) by 480 days.

(21) Appl. No.: 13/924,053

(22) Filed: Jun. 21, 2013

(65) Prior Publication Data

US 2014/0375171 A1   Dec. 25, 2014

(51) Int. Cl.
| | |
|---|---|
| *H01L 41/25* | (2013.01) |
| *H01L 41/08* | (2006.01) |
| *B06B 1/06* | (2006.01) |
| *A61B 8/00* | (2006.01) |
| *A61B 8/08* | (2006.01) |

(52) U.S. Cl.
CPC ............ *H01L 41/0825* (2013.01); *B06B 1/067* (2013.01); *B06B 1/0622* (2013.01); *B06B 1/0681* (2013.01); *H01L 41/25* (2013.01); *A61B 8/4483* (2013.01); *A61B 8/483* (2013.01); *Y10T 29/42* (2015.01)

(58) Field of Classification Search
CPC .... B06B 1/0622; B06B 1/0603; G10K 11/02; G10K 11/30; H04R 17/00; H03H 3/04; H01L 41/053
USPC .......................... 310/341, 334, 335, 322, 346
See application file for complete search history.

(56) References Cited

U.S. PATENT DOCUMENTS

| | | | |
|---|---|---|---|
| 2004/0095045 A1* | 5/2004 | Baumgartner | ............ B06B 1/06 310/365 |
| 2005/0131299 A1 | 6/2005 | Freeman et al. | |
| 2006/0184035 A1 | 8/2006 | Kimura et al. | |
| 2007/0276248 A1* | 11/2007 | Saito | ...................... A61B 8/546 600/459 |
| 2009/0062656 A1* | 3/2009 | Hyuga | ..................... A61B 8/12 600/459 |
| 2009/0069689 A1* | 3/2009 | Isono | .................... B06B 1/0629 600/459 |

(Continued)

FOREIGN PATENT DOCUMENTS

EP           1879024 A1     1/2008

OTHER PUBLICATIONS

International Search Report and Written Opinion for PCT/US2014/043209, mail date Dec. 22, 2014, 11 pages.

*Primary Examiner* — Shawki S Ismail
*Assistant Examiner* — Bryan Gordon
(74) *Attorney, Agent, or Firm* — Dean D. Small; The Small Patent Law Group, LLC

(57) ABSTRACT

An ultrasound transducer includes an acoustic layer having a front side and an opposite back side. The acoustic layer is configured to convert electrical signals into ultrasound waves to be transmitted from the front side toward a target. The acoustic layer is configured to convert received ultrasound waves into electrical signals. A lens is connected to the front side of the acoustic layer. A heat sink is connected to the back side of the acoustic layer. A flex circuit is disposed between the acoustic layer and the heat sink. The flex circuit includes a backside matching layer incorporated into a body of the flex circuit. The backside matching layer is connected in thermal communication with the acoustic layer and the heat sink such that the backside matching layer is configured to conduct heat from the acoustic layer to the heat sink.

20 Claims, 7 Drawing Sheets

(56) References Cited

U.S. PATENT DOCUMENTS

2012/0007471 A1* 1/2012 Tai ..................... B06B 1/067 310/334

2012/0007472 A1 1/2012 Tai et al.
2012/0313486 A1 12/2012 Jung et al.

* cited by examiner

ULTRASOUND TRANSDUCER AND METHOD FOR MANUFACTURING AN ULTRASOUND TRANSDUCER

BACKGROUND OF THE INVENTION

The subject matter disclosed herein relates generally to ultrasound systems, and more particularly to ultrasound transducers and methods for manufacturing ultrasound transducers.

Ultrasound systems typically include ultrasound scanning devices (e.g., an ultrasound transducer housed within a probe) that perform various ultrasound scans (e.g., imaging a body or other volume). The scanning devices include acoustic elements that transmit and receive ultrasound signals. The ultrasound signals received by the acoustic elements are used to generate an image of the body or other volume. For example, the received ultrasound signals may be used to generate an image of internal tissues of a patient, such as, but not limited to, an image of a patient's heart.

But, transmitting ultrasound signals from the acoustic elements can heat a lens of the scanning device that physically contacts the patient. The lens of scanning devices typically has a maximum surface temperature of approximately 40 degrees Celsius in order to avoid patient discomfort and comply with regulatory temperature limits. Thus, lens temperature can be a limiting factor for performance of the scanning device.

BRIEF DESCRIPTION OF THE INVENTION

In an embodiment, an ultrasound transducer includes an acoustic layer having a front side and an opposite back side. The acoustic layer is configured to convert electrical signals into ultrasound waves to be transmitted from the front side toward a target. The acoustic layer is configured to convert received ultrasound waves into electrical signals. A lens is connected to the front side of the acoustic layer. A heat sink is connected to the back side of the acoustic layer. A flex circuit is disposed between the acoustic layer and the heat sink. The flex circuit includes a backside matching layer incorporated into a body of the flex circuit. The backside matching layer is connected in thermal communication with the acoustic layer and the heat sink such that the backside matching layer is configured to conduct heat from the acoustic layer to the heat sink.

In an embodiment, a method is provided for manufacturing an ultrasound transducer. The method includes providing a completed flex circuit that includes a backside matching layer incorporated into a body of the flex circuit. The method also includes assembling the ultrasound transducer using the completed flex circuit. Assembling the ultrasound transducer includes connecting a lens to a front side of an acoustic layer, connecting the flex circuit to a back side of the acoustic layer, and connecting a heat sink to the flex circuit such that the backside matching layer of the flex circuit is connected in thermal communication between the back side of the acoustic layer and the heat sink for conducting heat from the acoustic layer to the heat sink.

In an embodiment, an ultrasound transducer includes an acoustic layer having a front side and an opposite back side. The acoustic layer is configured to convert electrical signals into ultrasound waves to be transmitted from the front side toward a target. The acoustic layer is configured to convert received ultrasound waves into electrical signals. The ultrasound transducer includes a lens connected to the front side of the acoustic layer, and a heat sink connected to the back side of the acoustic layer. The ultrasound transducer includes a flex circuit disposed between the acoustic layer and the heat sink. The flex circuit has a body that includes first and second dielectric coverlaps and an electrical signal layer disposed between the first and second dielectric coverlaps. The body also includes a backside matching layer disposed within the body between the electrical signal layer and the second dielectric coverlap. The backside matching layer is connected in thermal communication with the acoustic layer and the heat sink such that the backside matching layer is configured to conduct heat from the acoustic layer to the heat sink.

DETAILED DESCRIPTION OF THE INVENTION

Figure 1:
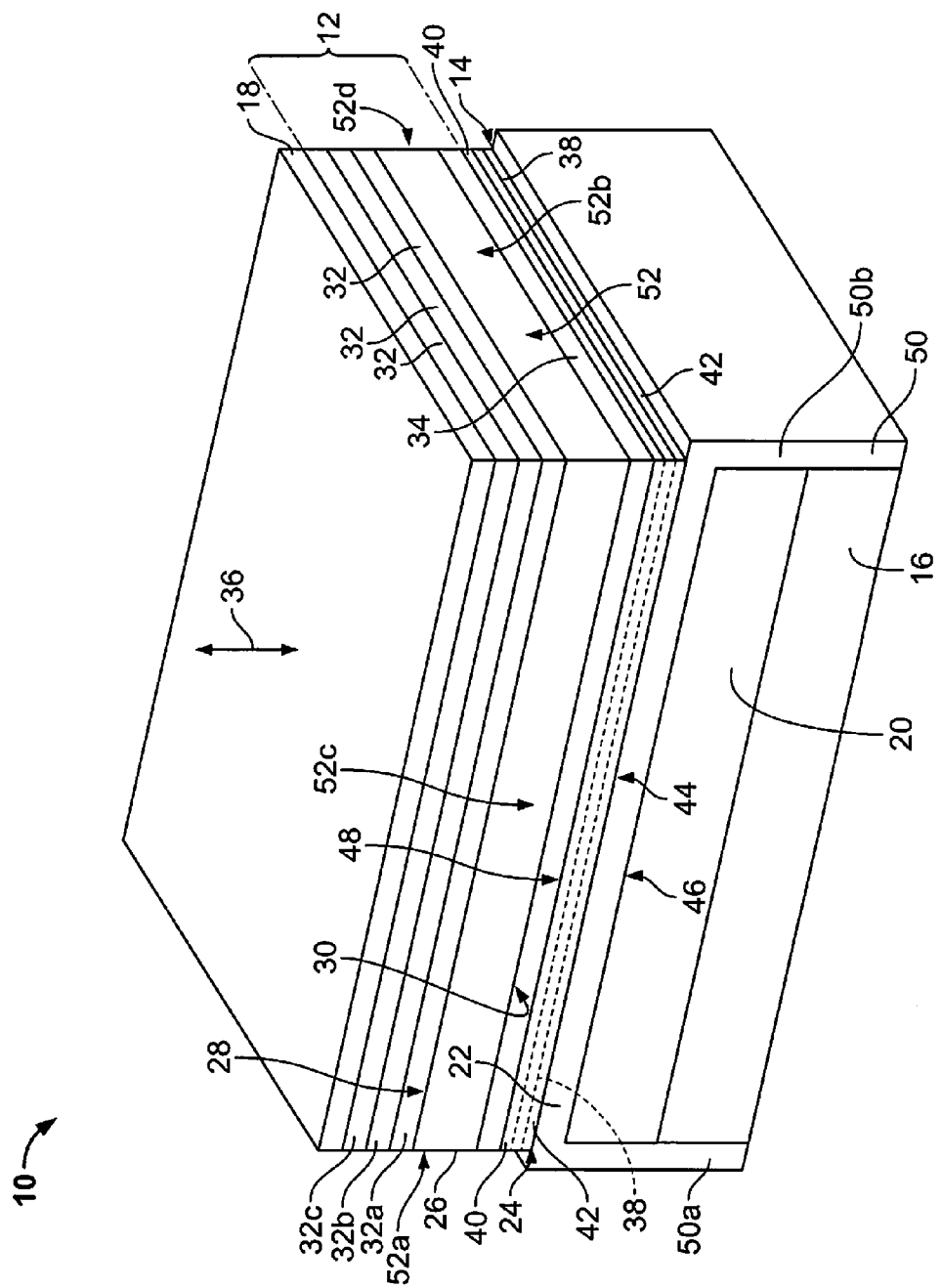
FIG. 1 is a perspective view of an ultrasound transducer formed in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and/or the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide ultrasound transducers and methods for manufacturing ultrasound transducers. An ultrasound transducer in accordance with various embodiments includes an acoustic layer having a front side and an opposite back side. The acoustic layer is configured to convert electrical signals into ultrasound waves to be transmitted from the front side toward a target. The acoustic layer is configured to convert received ultrasound waves into electrical signals. A lens is connected to the front side of the acoustic layer. A heat sink is connected to the back side of the acoustic layer. A flex circuit is disposed between the acoustic layer and the heat sink. The flex circuit includes a backside matching layer incorporated into a body of the flex circuit. The backside matching layer is connected in thermal communication with the acoustic layer and the heat sink such that the backside matching layer is configured to conduct heat from the acoustic layer to the heat sink.

A technical effect of at least some embodiments is more effective thermal management and/or increased acoustic performance as compared to at least some known ultrasound transducers. A technical effect of at least some embodiments is an ultrasound transducer that is less costly to manufacture as compared to at least some known ultrasound transducers.

Figure 2:
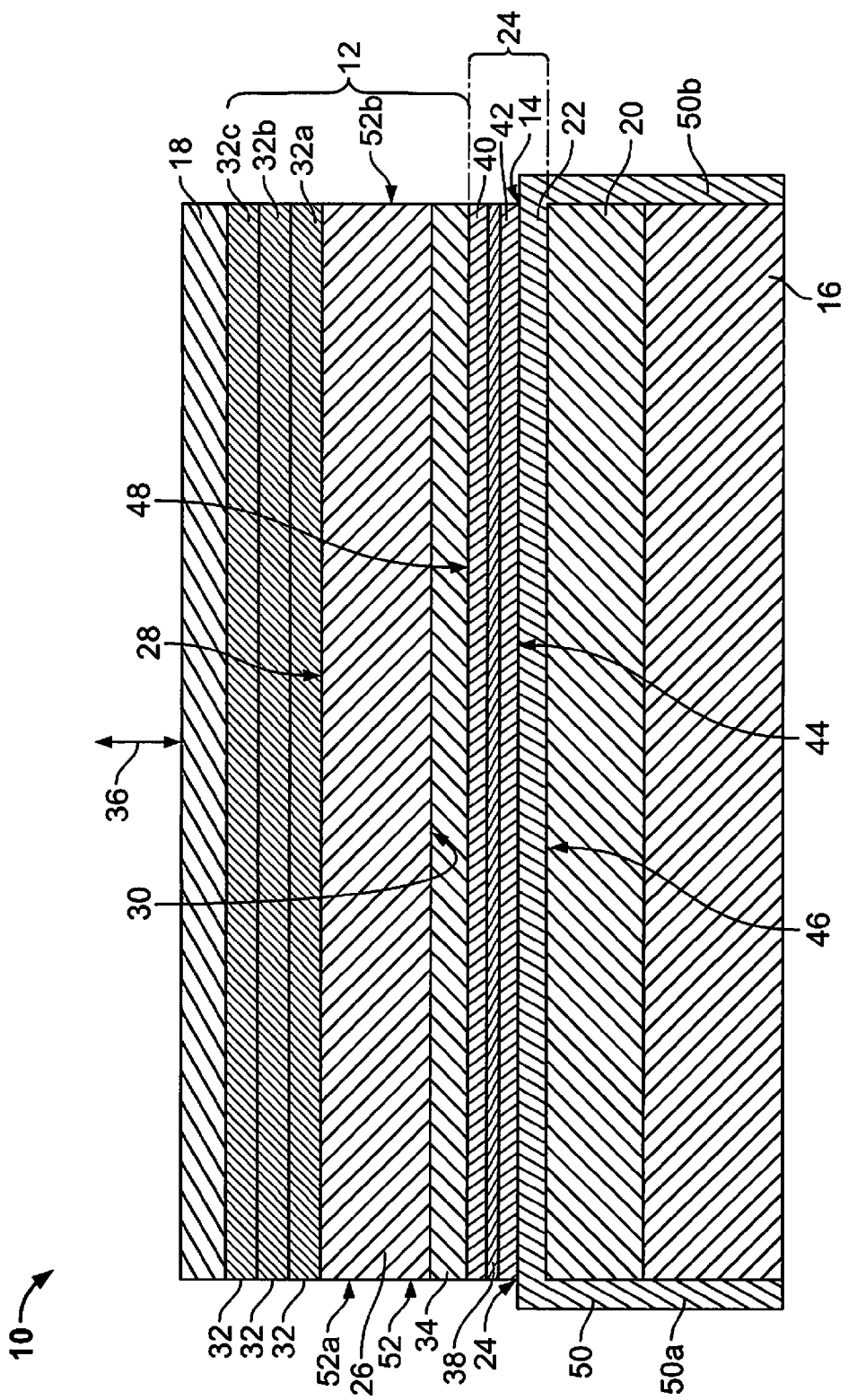
FIG. 2 is a cross-sectional view of the ultrasound transducer shown in FIG. 1.

FIG. 1 is a perspective view of a portion of the ultrasound transducer 10 formed in accordance with various embodiments. FIG. 2 is a cross-sectional view of the ultrasound transducer 10. The ultrasound transducer 10 includes an acoustic element 12, a flex circuit 14, and a heat sink 16. The ultrasound transducer 10 may also include other layers, such as, but not limited to, a lens 18 and/or a backing 20. The backing 20 may be a relatively high acoustic attenuation material to dampen backside acoustic energy. The flex circuit 14 is electrically connected to the acoustic element 12 to provide an electrical connection between the acoustic element 12 and one or more other components of an ultrasound system (e.g., the ultrasound system 310 shown in FIG. 5). For example, the flex circuit 14 may provide an electrical connection between the acoustic element 12 and an integrated circuit (not shown), an RF processor (e.g., the RF processor 322 shown in FIG. 5), a memory (e.g., the memory 324 and/or the memory 332 shown in FIG. 5), a signal processor (e.g., the signal processor 326 shown in FIG. 5), a user input (e.g., the user input 330 shown in FIG. 5), and/or a display system (e.g., the display system 328 shown in FIG. 5). As will be described in more detail below, the flex circuit 14 includes a backside matching layer 22 that is incorporated into a body 24 of the flex circuit 14.

In the illustrated embodiment, the acoustic element 12, the flex circuit 14, and the heat sink 16 are arranged in a stack, as can be seen in FIGS. 1 and 2. Within the stack, the flex circuit 14 is disposed between the acoustic element 12 and the heat sink 16. Other relative arrangements of the acoustic element 12, the flex circuit 14, and the heat sink 16 may be provided in addition or alternative to the illustrated stack.

Although only a single acoustic element 12 is shown herein, the acoustic element 12 is optionally arranged in an array with a plurality of other acoustic elements 12. The array of acoustic elements 12 are optionally electrically connected to a single flex circuit 14 for providing the electrical connection between the acoustic elements 12 and the integrated circuit and/or other ultrasound processing equipment. Moreover, the array of acoustic elements 12 are optionally connected in thermal communication with a single heat sink 16 for conducting heat from the acoustic elements 12. The array of acoustic elements 12 may be arranged in a one dimensional (1D) array, a 1.5D array, a 1.75D array, a two-dimensional (2d) array, and/or the like. A variety of geometries may also be used, such as, but not limited to, linear, curved, cylindrical, and/or the like.

Each acoustic element 12 includes an acoustic layer 26 that is configured to generate and transmit acoustic energy into a target (i.e., a body and/or other volume) and receive backscattered acoustic signals from the target to create and display an image. In other words, the acoustic layer 26 is configured to convert electrical signals into ultrasound waves to be transmitted from a front side 28 of the acoustic layer toward the target, and the acoustic layer 26 is configured to convert received ultrasound waves into electrical signals. The acoustic layer 26 may have any value of acoustic impedance, such as, but not limited to, between approximately 3 MRayls and approximately 35 MRayls. The acoustic layer 26 may include electrodes (not shown) for electrical connection.

The acoustic layer 26 may be any type of acoustic layer that is formed from any material(s), such as, but not limited to, a piezoelectric ceramic (e.g., lead zirconate titanate (PZT), lead magnesium niobate-lead titanite (PMN-PT), and/or the like), a piezocomposite, piezoelectric crystals, a piezoelectric single crystal, a piezopolymer, and/or the like. In some embodiments, the acoustic layer 26 may include more than one sub-layer of one material or of two or more different materials. In other words, in some embodiments, the acoustic layer 26 may include multiple sub-layers of the same material, while in other embodiments the acoustic layer 26 may include multiple layers of different materials.

The acoustic layer 26 includes the front side 28 and a back side 30 that is opposite the front side 28. For purposes of this disclosure, the front side 28 of the acoustic layer 26 is defined to include the side of the acoustic layer 26 from which ultrasound waves are emitted towards the lens 18. The back side 30 of the acoustic layer 26 is defined to include the side of the acoustic layer 26 that is opposite of the front side 28 and that faces away from the lens 18.

As can be seen in FIGS. 1 and 2, the heat sink 16 is connected to the back side 30 of the acoustic layer 26. The heat sink 16 is indirectly connected to the back side 30 of the acoustic layer 26 through the flex circuit 14 and the optional backing 20. As used herein, the term "indirectly connected" is defined to include two structures connected to each other through one or more additional structures and/or components.

The lens 18 is connected to the front side 28 of the acoustic layer 26. The acoustic element 12 may include one or more other layers in addition to the acoustic layer 26. For example, the acoustic element 12 may include one or more frontside matching layers 32, one or more conductive film layers (not shown), and/or one or more dematching layers 34. Each acoustic element 12 may include any number of layers overall. In the illustrated embodiment, the acoustic element 12 includes three frontside matching layers 32a, 32b, and 32c. But, each acoustic element 12 may include any number of frontside matching layers 32. For example, some embodiments may include only one front side matching layer 32, while other embodiments may include only two or four or more frontside matching layers 32.

The lens 18 is indirectly connected to the front side 28 of the acoustic layer 26 through the frontside matching layers 32, which are disposed between the acoustic layer 26 and the lens 18. In some embodiments, the frontside matching layers 32, the acoustic layer 26, and the lens 18 are bonded together using epoxy and/or other adhesive material (e.g., cured under pressure), such as, but not limited to, a material supplied by tooling including a press machine and/or the like. Arrows 36 depict ultrasound waves transmitted from and received at ultrasound transducer 10.

The frontside matching layers 32 are disposed between the acoustic layer 26 and the lens 18 to increase the energy of the waves transmitted from the ultrasound transducer 10. The acoustic impedance of each frontside matching layer 32 may be selected to reduce the mismatch of acoustic impedances between the acoustic layer 26 and the lens 18. The frontside matching layers 32 may result in less reflection and/or refraction of ultrasound waves between the acoustic layer 26 and the lens 18.

The lens 18 and the acoustic layer 26 may each have any acoustic impedance. For example, in some embodiments the lens 18 has an acoustic impedance of approximately 1.5 MRayl and the acoustic layer 26 has an acoustic impedance of approximately 30 MRayl. Other examples include, but are not limited to, embodiments wherein the lens 18 has an acoustic impedance anywhere in the range of approximately 1.2 MRayl to approximately 1.6 MRayl and the acoustic layer 26 has an acoustic impedance anywhere in the range of approximately 20 MRayl to approximately 40 MRayl.

Each frontside matching layer 32 may have any value of acoustic impedance, such as, but not limited to, between approximately 1 MRayl and approximately 20 MRayl, between approximately 5 MRayl and approximately 15 MRayl, less than approximately 16 MRayl, between approximately 2 MRayl and approximately 8 MRayl, less than approximately 9 MRayl, among others. In the illustrated embodiment, the frontside matching layer 32a has an acoustic impedance of approximately 10-20 MRayl, the frontside matching layer 32b has an acoustic impedance of approximately 5-15 MRayl, and the frontside matching layer 32c has an acoustic impedance of approximately 2-8 MRayl. In some embodiments, each frontside matching layer 32 has an acoustic impedance that is less than the acoustic impedance of the acoustic layer 26.

In embodiments wherein the acoustic element 12 includes a plurality of the frontside matching layers 32, the frontside matching layers optionally provide a progressive reduction in acoustic impedance from the acoustic layer 26. For example, in some embodiments, the frontside matching layer 32 closest to the acoustic layer 26 (e.g., the frontside matching layer 32a) is approximately 15 MRayl, the next frontside matching layer 32 (e.g., the frontside matching layer 32b) is approximately 8 MRayl, and the frontside matching layer 32 farthest from the acoustic layer 26 (e.g., the frontside matching layer 32c) is approximately 3 MRayl. Optionally, each of the frontside matching layers 32 has a relatively high thermal conductivity, such as, but not limited to, greater than approximately 30 W/mK.

Each frontside matching layer 32 may have any thickness and the frontside matching layers 32 may have any combined thickness. One example of a thickness of a frontside matching layer 32 includes a thickness of approximately ¼ or less of the wavelength at the resonant frequency of the ultrasound transducer 10. But, a frontside matching layer 32 may be more than approximately ¼ of the wavelength at the resonant frequency of the ultrasound transducer 10. For example, one or more of the frontside matching layers 32 may be approximately ½ of the wavelength at the resonant frequency. In some embodiments, each of the frontside matching layers 32 is approximately ¼ of the desired wavelength or less in order to minimize destructive interference caused by waves reflected from the boundaries between each of the frontside matching layers 32.

Each of the frontside matching layers 32 may be any type of matching layer that is formed from any material(s) that enables the frontside matching layer 32 to function as described and/or illustrated herein, such as, but not limited to, an epoxy, a filled epoxy that is filled with one or more different fillers, metal-impregnated graphite, glass ceramic, composite ceramic, metal (such as, but not limited to, copper, copper alloy, copper with graphite pattern embedded therein, magnesium, magnesium alloy, aluminum, aluminum alloy, and/or the like), and/or the like. Any fillers that are used (e.g., with a filled epoxy) are optionally used to adjust the acoustic impedance of the frontside matching layer 32.

Each frontside matching layer 32 may be electrically conductive or electrically non-conductive. When a frontside matching layer 32 is electrically non-conductive, the frontside matching layer 32 optionally includes a conductive film layer (not shown) thereon. One or more frontside matching layers 32 (and/or a conductive film layer thereon) may provide an electrical ground connection for the acoustic element 12.

The dematching layer 34 of the acoustic element 12 is disposed between the back side 30 of the acoustic layer 26 and the flex circuit 14. The dematching layer 34 has a higher acoustic impedance than the acoustic layer 26 to increase the power of the ultrasound waves transmitted to the lens 18. The dematching layer 34 has a relatively high acoustic impedance and functions to clamp the acoustic layer 26 so that most of the acoustic energy is transmitted out through the front side 28 of the acoustic layer 26. In the illustrated embodiment, the acoustic element 12 includes a single dematching layer 34. But, the acoustic element 12 may include any number of dematching layers 34, for example two or more dematching layers 34. Moreover, the dematching layer 34 is optional such that, in some embodiments, the acoustic element 12 does not include any dematching layers 34.

In the illustrated embodiment, the flex circuit 14 is indirectly connected to the back side 30 of the acoustic layer 26 through the dematching layer 34. But, in embodiments wherein the acoustic element 12 does not include any dematching layers 34, the flex circuit 14 may be directly connected to the back side 30 of the acoustic layer 26. In some embodiments, the acoustic layer 26, the dematching layer(s) 34 (if included), and the flex circuit 14 are bonded together with a thermally conductive material (not shown), such as, but not limited to, an epoxy with thermally conductive additives, a thermally conductive adhesive, and/or the like.

The dematching layer 34 may have any value of acoustic impedance, such as, but not limited to, between approximately 40 MRayl and approximately 120 MRayl, between approximately 60 MRayl and approximately 100 MRayl, greater than approximately 70 MRayl, and/or the like. The dematching layer 34 may have relatively good thermal conductivity that can carry over, or transfer, heat generated by the acoustic layer 26 to the flex circuit 14.

The dematching layer 34 may be any type of dematching layer that is formed from any material(s), such as, but not limited to, metal, a carbide alloy and/or compound material (e.g., zirconium, tungsten, silicon, titanium, tantalum carbide, and/or the like) and/or the like. The dematching layer 34 may have any thickness, which may depend on the frequency of the ultrasound transducer 10. Examples of the thickness of the dematching layer 34 include, but are not limited to, between approximately 50 um and approximately 350 um. The dematching layer 34 may be laminated to the acoustic layer 26 using any suitable method, structure, process, means, and/or the like, such as, but not limited to, using epoxy having an exemplary thickness of less than approximately 5 um.

In some embodiments, the dematching layer 34 is coated with an electrically conductive coating (not shown) of metal and/or another electrical conductor. The electrically conductive coating may facilitate electrical connection between the dematching layer 34 and the flex circuit 14. The dematching layer 34 may be coated with the electrically conductive coating using any suitable method, structure, process, means, and/or the like. One example of forming the electrically conductive coating on the dematching layer 34 is to first sputter with Ni or Cr material as a seed layer (e.g., less than approximately 0.1 um) and then add a layer of gold (e.g., less than approximately 1 um). The layer of gold may then be electroplated or electrolysis with Ni (e.g., less than approximately 5 um) and gold (e.g., less than approximately 0.2 um) on the outside to prevent oxidation. In some embodiments, and in addition or alternatively to the electrically conductive coating on the dematching layer 34, the acoustic element 12 may be provided with electrical contacts (not shown; and having any other structure than the electrically conductive coating) for electrical connection with the flex circuit 14. Such electrical contacts of the acoustic element 12 may be, but are not limited to, solder pads, solder bumps, stud bumps, plated bumps, and/or the like.

The flex circuit 14 includes the body 24, which includes the backside matching layer 22, an electrical signal layer 38, and a pair of dielectric coverlaps 40 and 42. The flex circuit 14 may include other layers, such as, but not limited to, one or more interior dielectric layers (e.g., the interior dielectric layer 154 shown in FIG. 3), and/or the like. At least some of the various layers of the flex circuit 14 (e.g., the layers 22, 38, 40, 42, any interior dielectric layers, and/or the like) are optionally bonded together using epoxy and/or other adhesive material (e.g., cured under pressure), such as, but not limited to, a material supplied by tooling including a press machine and/or the like.

The flex circuit 14 includes one or more electrical contacts (not shown) for electrically connecting the flex circuit 14 to the acoustic element 12. The electrical signal layer 38 includes one or more electrical paths (not shown) electrically connected to the electrical contact(s). The electrical path(s) of the electrical signal layer 38 electrically connects the acoustic element 12 to one or more other components of an ultrasound system (e.g., the ultrasound system 310 shown in FIG. 5). For example, the electrical signal layer 38 may provide signal, ground, control, and/or power connections between the acoustic element 12 and an integrated circuit (not shown), an RF processor (e.g., the RF processor 322 shown in FIG. 5), a memory (e.g., the memory 324 and/or the memory 332 shown in FIG. 5), a signal processor (e.g., the signal processor 326 shown in FIG. 5), a user input (e.g., the user input 330 shown in FIG. 5), and/or a display system (e.g., the display system 328 shown in FIG. 5). The electrical signal layer 38 may be fabricated from any materials, such as, but not limited to, one or more metals, one or more metal alloys, copper, copper alloy, gold, gold alloy, silver, silver alloy, one or more non-metallic electrical conductors, and/or the like.

The dielectric coverlaps 40 and 42 and any interior dielectric layers of the flex circuit 14 may each be fabricated from any materials, such as, but not limited to, polyimide (e.g., Kapton®), a relatively low acoustic impedance material (e.g., an acoustic impedance of less than approximately 10 MRayl), an organic material, and/or the like. Each of the dielectric coverlaps 40 and 42 may be referred to herein as a "first" and/or a "second" dielectric coverlap.

The body 24 of the flex circuit 14 is generally flexible such that the flex circuit 14 is a flexible circuit. In some embodiments, the flex circuit 14 is a cable that electrically connects the acoustic element 12 to other components of the ultrasound system. In some embodiments wherein the flex circuit 14 is a cable, the flex circuit 14 is a flat flexible cable, which is sometimes referred to as a "flat flex circuit", a "flat flexible conductor cable", a "flex cable", a "cable flex circuit", and/or a "flexible flat cable". The body 24 of the flex circuit 14 may have any acoustic impedance, such as, but not limited to less than approximately 10 MRayl and/or between approximately 2 MRayl and approximately 15 MRayl. The body 24 of the flex circuit 14 may have any thickness, such as, but not limited to, approximately 100 μm or less, and/or the like.

As described above, the backside matching layer 22 is incorporated into the body 24 of the flex circuit 14. In the illustrated embodiment of FIGS. 1 and 2, the backside matching layer 22 is an exterior layer of the body 24 of the flex circuit 14. Specifically, the dielectric coverlap 40 of the body 24 extends between the electrical signal layer 38 of the body 24 and the acoustic layer 26, while the dielectric coverlap 42 extends between the electrical signal layer 38 and the heat sink 16. The backside matching layer 22 is laminated to a heat sink side 44 of the dielectric coverlap 42. Accordingly, and as can be seen in FIGS. 1 and 2, the backside matching layer 22 is an exterior layer of the body 24 that extends between the dielectric coverlap 42 and the heat sink 16. The backside matching layer 22 thus defines an exterior heat sink side 46 of the body 24 of the flex circuit 14 that faces the heat sink 16, as illustrated in FIGS. 1 and 2. In the illustrated embodiment of FIGS. 1 and 2, the body 24 of the flex circuit 14 includes an exterior acoustic layer side 48 that is opposite the heat sink side 46. As can be seen in FIGS. 1 and 2, the acoustic layer side 48 of the body 24 faces the acoustic layer and is defined by the dielectric coverlap 40.

The backside matching layer 22 may be laminated to the heat sink side 44 of the dielectric coverlap 42 using any suitable lamination process, using structure, using means, and/or the like. The backside matching layer 22 is optionally laminated to the heat sink side 44 of the dielectric coverlap 42 using epoxy and/or other adhesive material (e.g., cured under pressure), such as, but not limited to, that supplied by tooling including a press machine and/or the like. In some embodiments, the backside matching layer 22 is laminated to the heat sink side 44 of the dielectric coverlap 42 using a thermally conductive material (not shown), such as, but not limited to, an epoxy with thermally conductive additives, a thermally conductive adhesive, and/or the like.

When the backside matching layer 22 is incorporated into the body 24 of the flex circuit 14 as shown in FIGS. 1 and 2 and described above (i.e., once the backside matching layer 22 has been laminated to the dielectric coverlap 42 and the remainder of the body 24 has been formed), the flex circuit 14 is a completed flex circuit 14. The ultrasound transducer 10 can then be assembled using the completed flex circuit 14. For example, a supplier may supply the completed flex circuit 14 to a different manufacturing entity that manufactures (i.e., assembles) the ultrasound transducer 10 using the completed flex circuit 14. It should be understood that the manufacturing entity may perform various operations on the completed flex circuit 14 to assemble the ultrasound transducer 10 using the completed flex circuit 14, such as, but not limited to, terminating one or more electrical paths of the completed flex circuit 14, trimming a length of the flex circuit, and/or the like.

In alternative to assembling the ultrasound transducer 10 using a completed flex circuit 14, the backside matching layer 22 may be laminated to the heat sink 16 (e.g., to the backing 20 if included or directly to the heat sink 16) before the backside matching layer 22 is laminated to the dielectric coverlap 42.

The backside matching layer 22 may be fabricated from any materials that enable the backside matching layer 22 to function as described and/or illustrated herein, such as, but not limited to, aluminum, aluminum alloy, copper, copper alloy, other metals, other metal alloys, other thermally conductive materials, and/or the like.

The backside matching layer 22 is indirectly connected to the acoustic layer 26 through the dematching layer 34 and the remainder (i.e., the coverlap 40, the electrical signal layer 38, any interior dielectric layers of the body 24, and the coverlap 42) of the body 24 of the flex circuit 14. The backside matching layer 22 is connected in thermal communication with the acoustic layer 26 and the heat sink 16 such that the backside matching layer 22 is configured to conduct heat from the acoustic layer 26 to the heat sink 16. Specifically, heat is conducted from the back side 30 of the acoustic layer 26, through the dematching layer 34, and through the remainder (i.e., the coverlap 40, the electrical signal layer 38, any interior dielectric layers of the body 24, and the coverlap 42) of the body 24 of the flex circuit 14 to the backside matching layer 22. Even though the flex circuit 14 includes the electrical signal layer 38 with the dielectric coverlaps 40 and 42, heat is still effectively transferred from the dematching layer 34 through the remainder (i.e., the coverlap 40, the electrical signal layer 38, any interior dielectric layers of the body 24, and the coverlap 42) of the body 24 of the flex circuit 14 to the backside matching layer 22 due to the thinness of the remainder of the body 24.

Even though the dematching layer 34 eliminates a relatively large percentage of the acoustic energy emitted from the back side 30 of the acoustic layer 26, some acoustic energy may still be transmitted through the dematching layer 34 and the flex circuit 14 (including through the backside matching layer 22). To damp such acoustic energy, the ultrasound transducer 10 optionally includes the thermal backing 20. The thermal backing 20 is fabricated from a material having a relatively high acoustic attenuation so that the thermal backing 20 can attenuate ultrasound waves from the acoustic layer 26. For example, the thermal backing 20 may be made of epoxy with a filler such as, but not limited to, titanium dioxide and/or the like. The thermal backing 20 may have any thickness, such as, but not limited to, approximately 2 mm thick, from 1 mm to approximately 20 mm thick, among others. In embodiments wherein the thermal backing 20 is fabricated from an epoxy with a filler of a higher thermal conductivity than the epoxy, the combination of the epoxy and the filler of the thermal backing 20 may have a relatively moderate or relatively low thermal conductivity, for example less than or equal to approximately 20 W/mK.

The heat sink 16 is connected to the thermal backing 20 such that the thermal backing 20 extends between the flex circuit 14 and the heat sink 16. The heat sink 16 includes a material with a relatively high specific heat capacity, such as, but not limited to, aluminum, aluminum alloy, copper, copper alloy, and/or the like. Because heat is not effectively conducted through the thermal backing 20, the backside matching layer 22 optionally includes one or more wings 50 that extend beyond a corresponding end 52 of the acoustic layer 26. In the illustrated embodiment of FIGS. 1 and 2, the wings 50 are integral extensions of the backside matching layer 22 that are folded such that the wings 50 are engaged in physical contact with the heat sink 16. The wings 50 may be connected to the heat sink 16 by a thermally conductive epoxy, solder, and/or any other technique that results in a thermally conductive interface between the backside matching layer 22 and the heat sink 16. As used herein, the term "thermally conductive" is defined to include a conductive interface that transfers heat at a rate of at least approximately 10 W/mK. In some embodiments, the thermally conductive interface between the backside matching layer 22 and the heat sink 16 provides heat transfer at a rate of greater than approximately 20 W/mK.

The backside matching layer 22 may include any number of the wings 50. In the illustrated embodiment, the backside matching layer 22 includes two wings 50a and 50b that extend beyond corresponding ends 52a and 52b of the acoustic layer 26. But, in other embodiments the backside matching layer 22 may include three or more wings 50 or only a single wing 50. Moreover, in addition or alternative to the wings 50a and/or 50b, the backside matching layer 22 may include a wing 50 that extends beyond an end 52c (not visible in FIG. 2) and/or a wing 50 that extends beyond an end 52d (not visible in FIG. 2) of the acoustic layer 26. In embodiments wherein the backside matching layer 22 includes only a single wing 50, the single wing 50 may extend beyond any number of the ends 52a, 52b, 52c, and/or 52d. For example, a single continuous wing 50 may extend along an approximate entirety of the perimeter of the heat sink 16.

In addition or alternative to the exemplary wings 50 that are integral extensions of the backside matching layer 22, one or more wings 50 may be defined by a sheet (e.g., the sheets 156 shown in FIG. 3) that is a discrete component from the backside matching layer 22 that is thermally connected between the backside matching layer 22 and the heat sink 16.

Optionally, the ultrasound transducer 10 may include a plurality of major cuts (not shown) through the acoustic element 12 to provide electrical separation between portions of the acoustic element 12, for example to create the optional array of the acoustic elements 12 described above. Moreover, the ultrasound transducer 10 may include a plurality of minor cuts (not shown) through at least a portion of the acoustic element 12, for example to damp horizontal vibration.

Figure 3:
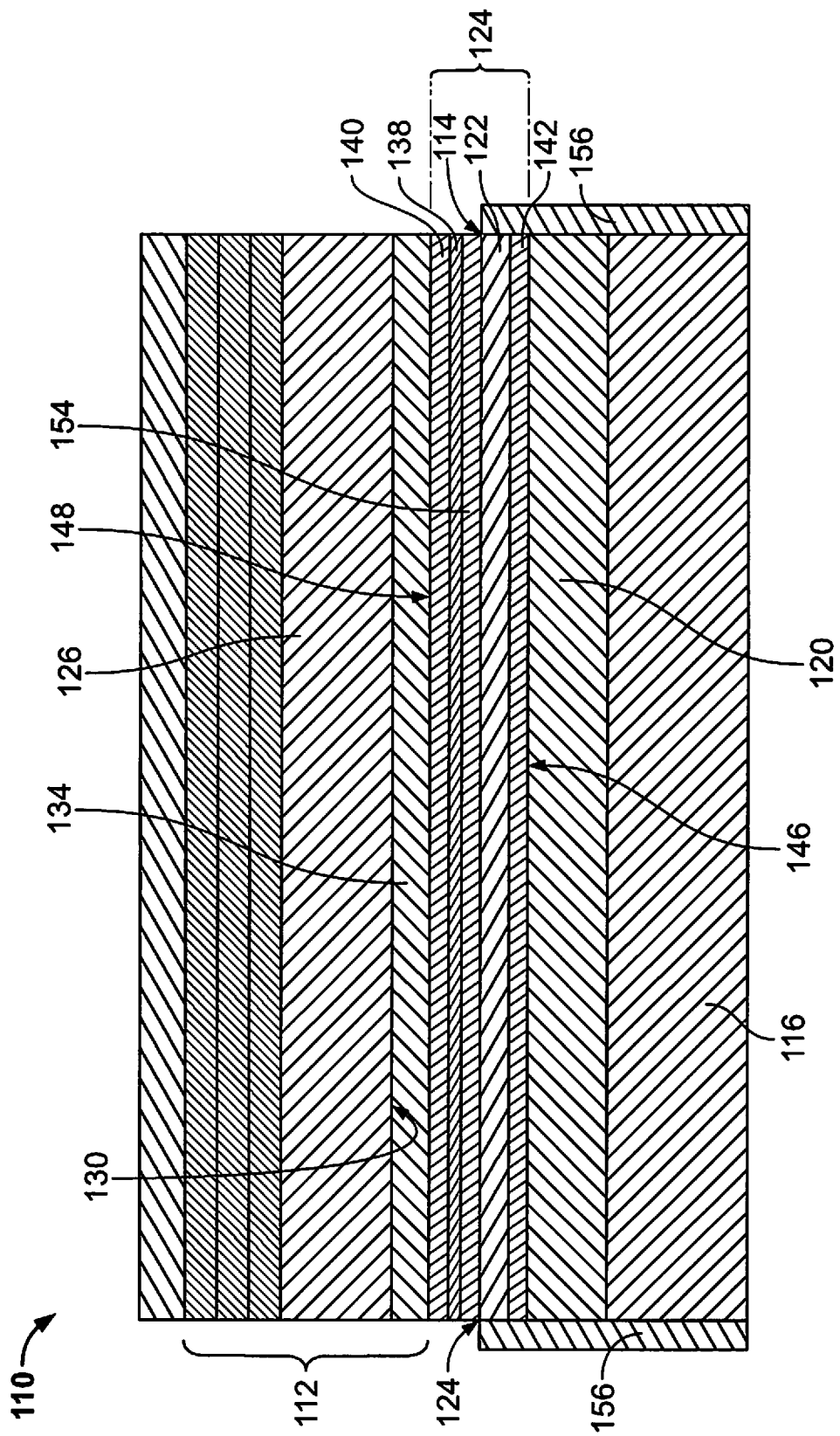
FIG. 3 is a cross-sectional view of another ultrasound transducer formed in accordance with various embodiments.

FIG. 3 is a cross-sectional view of another ultrasound transducer 110 formed in accordance with various embodiments. The ultrasound transducer 110 illustrates an embodiment wherein a backside matching layer 122 is incorporated into a body 124 of a flex circuit 114 as an interior layer of the body 124. The ultrasound transducer 110 includes an acoustic element 112, the flex circuit 114, and a heat sink 116.

The flex circuit 114 includes the body 124, which includes the backside matching layer 122, an electrical signal layer 138, and a pair of dielectric coverlaps 140 and 142. In the illustrated embodiment, the body 124 of the flex circuit 114 also includes an interior dielectric layer 154, and/or the like. At least some of the various layers of the flex circuit 114 (e.g., the layers 122, 138, 140, 142, 154, and/or the like) are optionally bonded together using epoxy and/or other adhesive material (e.g., cured under pressure), such as, but not limited to, a material supplied by tooling including a press machine and/or the like. In some embodiments, at least some of the various layers of the flex circuit 114 are bonded together using a thermally conductive material (not shown), such as, but not limited to, an epoxy with thermally conductive additives, a thermally conductive adhesive, and/or the like. Each of the dielectric coverlaps 140 and 142 may be referred to herein as a "first" and/or a "second" dielectric coverlap.

The backside matching layer 122 is incorporated into the body 124 of the flex circuit 114 as an interior layer of the body 124. Specifically, the backside matching layer 122 is disposed within the body 124 of the flex circuit 114 between the electrical signal layer 138 and the dielectric coverlap 142. More specifically, the electrical signal layer 138 is disposed within the body 124 between the dielectric coverlap 140 and the interior dielectric layer 154. The interior dielectric layer 154 is disposed within the body 124 between the electrical signal layer 138 and the backside matching layer 122, which is disposed within the body 124 between the interior dielectric layer 154 and the dielectric coverlap 142. Accordingly, and as can be seen in FIG. 3, the dielectric coverlaps 140 and 142 are exterior layers of the body 124 that define an exterior acoustic layer side 148 and an exterior heat sink side 146, respectively, of the body 124.

When the backside matching layer 122 is incorporated into the body 124 of the flex circuit 114 as shown in FIG. 3 and described above, the flex circuit 114 is a completed flex circuit 114. The ultrasound transducer 110 can then be assembled using the completed flex circuit 114. For example, a supplier may supply the completed flex circuit 114 to a different manufacturing entity that manufactures (i.e., assembles) the ultrasound transducer 110 using the completed flex circuit 114. It should be understood that the manufacturing entity may perform various operations on the completed flex circuit 114 to assemble the ultrasound transducer 110 using the completed flex circuit 114, such as, but not limited to, terminating one or more electrical paths of the completed flex circuit 114, trimming a length of the flex circuit, and/or the like.

The backside matching layer 122 is indirectly connected to an acoustic layer 126 of the acoustic element 112 through a dematching layer 134 of the acoustic element and through the coverlap 140, the electrical signal layer 138, and the interior dielectric layer 154 of the body 124 of the flex circuit 114. The backside matching layer 122 is connected in thermal communication with the acoustic layer 126 and the heat sink 116 such that the backside matching layer 122 is configured to conduct heat from the acoustic layer 126 to the heat sink 116. Specifically, heat is conducted from a back side 130 of the acoustic layer 126, through the dematching layer 134, and through the coverlap 140, the electrical signal layer 138, and the interior dielectric layer 154 of the body 124 to the backside matching layer 122.

The ultrasound transducer 110 includes an optional thermal backing 120. Because heat may not be effectively conducted through the thermal backing 120, the backside matching layer 122 is optionally thermally connected to the heat sink 116 through a thermally conductive sheet 156. Each thermally conductive sheet 156 is a discrete component from the backside matching layer 122 that is engaged in physical contact with both the backside matching layer 122 and the heat sink 116. The thermally conductive sheets 156 may be connected to the backside matching layer 122 and/or the heat sink 116 by a thermally conductive epoxy, solder, and/or any other technique that results in a thermally conductive interface between the backside matching layer 122 and the heat sink 116. In some embodiments, the thermally conductive sheets 156 are configured to provide heat transfer from the backside matching layer 122 to the heat sink 116 at a rate of greater than approximately 20 W/mK. The ultrasound transducer 110 may include any number of the thermally conductive sheets 156. In some alternative embodiments, the thermally conductive sheets 156 and the backside matching layer 122 are a continuous layer (such as, but not limited to, having a thickness of approximately 0.05 mm, approximately 0.1 mm, approximately 0.025 mm, and/or the like), that is folded (i.e., bent) over the thermal backing 120 (if included) and the heat sink 116, for example as is described and illustrated with respect to the ultrasound transducer 10. Such a one-piece construction of the thermally conductive sheets 156 and the backside matching layer 122 may reduce a cost, a difficulty, and/or a time of manufacturing the ultrasound transducer 110, for example as compared to at least some known ultrasound transducers.

Figure 4:
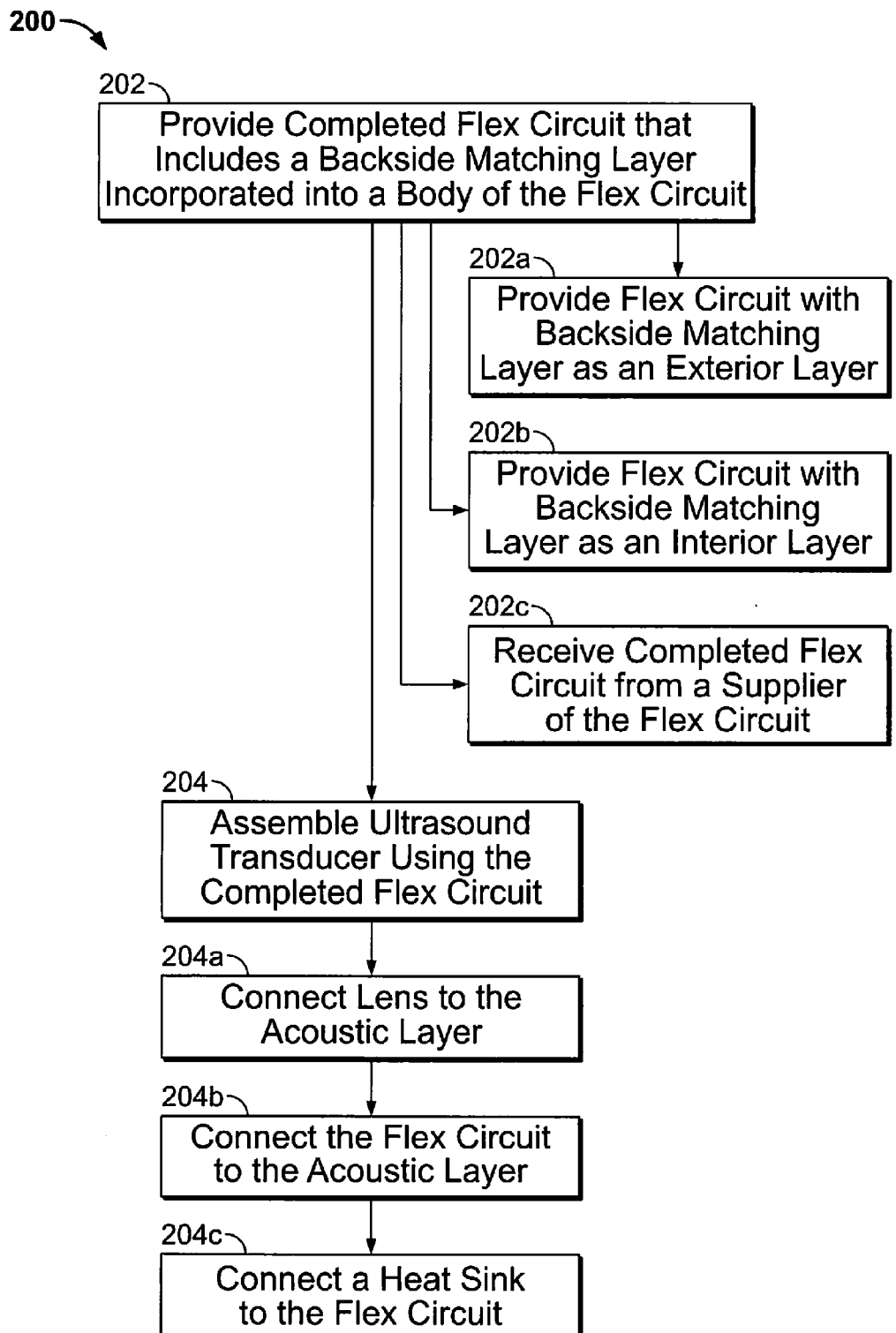
FIG. 4 is a flowchart illustrating a method for manufacturing an ultrasound transducer in accordance with various embodiments.

FIG. 4 is a flowchart illustrating a method 200 for manufacturing an ultrasound transducer in accordance with various embodiments. Exemplary uses of the method 200 include manufacturing the ultrasound transducer 10 shown in FIGS. 1 and 2 or the ultrasound transducer 110 shown in FIG. 3. The method 200 includes, at 202, providing a completed flex circuit that includes a backside matching layer incorporated into a body of the flex circuit. For example, providing at 202 the completed flex circuit may include providing, at 202*a*, the flex circuit (e.g., the flex circuit 14 shown in FIGS. 1 and 2) with the backside matching layer (e.g., the backside matching layer 22 shown in FIGS. 1 and 2) as an exterior layer of the body (e.g., the body 24 shown in FIGS. 1 and 2) of the flex circuit. In other embodiments, providing at 202 the completed flex circuit may include providing, at 202*b*, the flex circuit (e.g., the flex circuit 114 shown in FIG. 3) with the backside matching layer (e.g., the backside matching layer 122 shown in FIG. 3) as an interior layer of the body (e.g., the body 124 shown in FIG. 3) of the flex circuit. In some embodiments, providing at 202 the completed flex circuit includes receiving, at 202*c*, the completed flex circuit from a supplier of the flex circuit.

At 204, the method 200 includes assembling the ultrasound transducer using the completed flex circuit. Assembling at 204 the ultrasound transducer includes connecting, at 204*a*, a lens (e.g., the lens 18 shown in FIGS. 1 and 2) to a front side (e.g., the front side 28 shown in FIGS. 1 and 2) of an acoustic layer (e.g., the acoustic layer 26 shown in FIGS. 1 and 2 or the acoustic layer 126 shown in FIG. 3). Optionally, connecting at 204*a* the lens to the front side of the acoustic layer includes indirectly connecting the lens to the front side of the acoustic layer using one or more frontside matching layers (e.g., the frontside matching layers 32 shown in FIGS. 1 and 2) disposed between the acoustic layer and the lens.

Assembling at 204 the ultrasound transducer includes connecting, at 204*b*, the flex circuit to a back side (e.g., the back side 30 shown in FIGS. 1 and 2) or the back side 130 shown in FIG. 3) of the acoustic layer. Optionally, connecting at 204*b* the flex circuit to the back side of the acoustic layer includes indirectly connecting the flex circuit to the back side of the acoustic layer using one or more dematching layers (e.g., the dematching layer 34 shown in FIGS. 1 and 2 or the dematching layer 134 shown in FIG. 3) disposed between the acoustic layer and the flex circuit.

Assembling at 204 the ultrasound transducer includes connecting, at 204*c*, a heat sink (e.g., the heat sink 16 shown in FIGS. 1 and 2 or the heat sink 116 shown in FIG. 3) to the flex circuit such that the backside matching layer of the flex circuit is connected in thermal communication between the back side of the acoustic layer and the heat sink for conducting heat from the acoustic layer to the heat sink.

Although described as being formed in the order of step 204*a*, then step 204*b*, and finally step 204*c*, the steps 204*a*, 204*b*, and 204*c* of assembling at 204 the ultrasound transducer may be performed in any order relative to each other. For example, in some embodiments, the steps 204*a*, 204*b*, and 204*c* are performed in the order of step 204*b*, then step 204*c*, and finally step 204*a*. The order of the steps 204*a*, 204*b*, and 204*c* relative to each other may be selected according to the desire, requirements, need, and/or the like of manufacturing the ultrasound transducer, for example to reduce a cost, a difficulty, and/or a time of manufacturing the ultrasound transducer.

Figure 5:
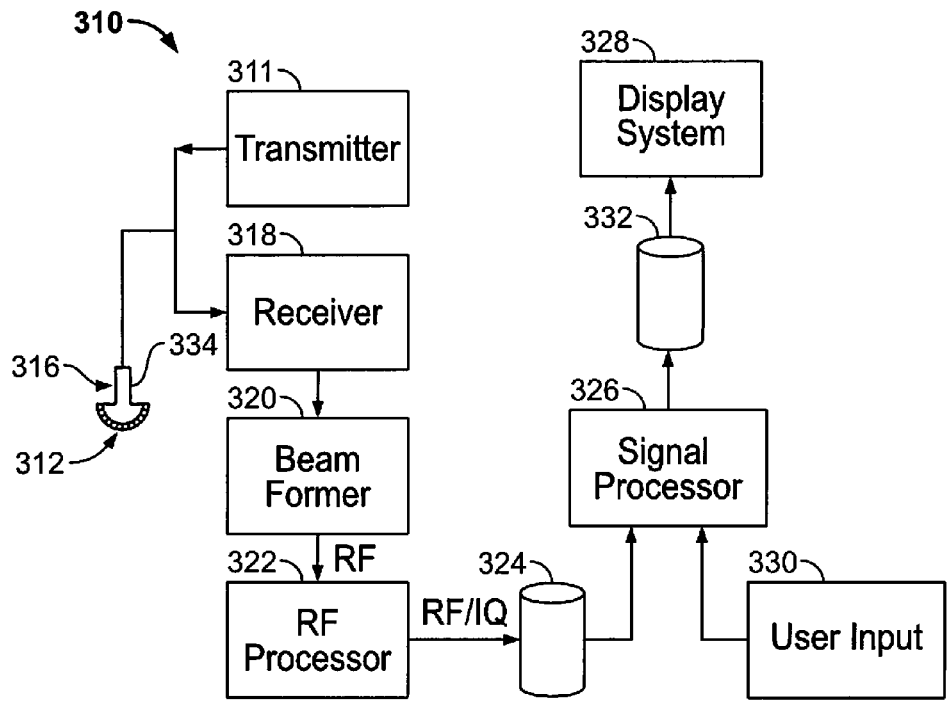
FIG. 5 is a block diagram of an ultrasound system in which various embodiments may be implemented.

FIG. 5 is a block diagram of an ultrasound system 310 in which various embodiments may be implemented. The ultrasound system 310 may be used, for example, to acquire ultrasound data and generate ultrasound images. The ultrasound system 310 includes a transmitter 311 that drives an array of acoustic elements 312 within or formed as part of an ultrasound transducer 316 to emit pulsed ultrasonic signals into a body or other volume. The ultrasonic signals are back-scattered from density interfaces and/or structures in the body or other volume (e.g., blood cells, fatty tissue, and/or muscular tissue in a body) to produce echoes that return to the acoustic elements 312. The echoes are received by a receiver 318. The received echoes are passed through beamforming electronics 320, which performs beamforming and outputs an RF signal. The RF signal then passes through an RF processor 322. The RF processor 322 may include a complex demodulator (not shown) that demodulates the RF signal to form IQ data pairs representative of the echo signals. The RF or IQ signal data may then be routed directly to a memory 324 for storage (e.g., temporary storage).

The ultrasound system 310 also includes a signal processor 326 to process the acquired ultrasound information (e.g., RF signal data or IQ data pairs) and prepare frames of ultrasound information for display on a display system 328. The signal processor 326 is adapted to perform one or more processing operations according to a plurality of selectable ultrasound modalities on the acquired ultrasound information. Acquired ultrasound information may be processed and/or displayed in real-time during a scanning session as the echo signals are received. Additionally or alternatively, the ultrasound information may be stored temporarily in the memory 324 during a scanning session and then processed and/or displayed in less than real-time in a live or off-line operation.

The signal processor 326 is connected to a user input device 330 that may control operation of the ultrasound system 310. The user input device 330 may be any suitable device and/or user interface for receiving user inputs to control, for example, the type of scan or type of transducer to be used in a scan. The display system 328 includes one or more monitors that present patient information, including diagnostic ultrasound images to the user for diagnosis and/or analysis. The ultrasound system 310 may include a memory 332 for storing processed frames of acquired ultrasound information that are not scheduled to be displayed immediately. One or both of the memory 324 and the memory 332 may store three-dimensional (3D) data sets of the ultrasound data, where such 3D datasets are accessed to present 2D and/or 3D images. Multiple consecutive 3D datasets may also be acquired and stored over time, such as to provide real-time 3D or 4D display. The images may be modified and/or the display settings of the display system 328 may be manually adjusted using the user input device 30.

In addition to the acoustic elements 312, various other components of the ultrasound system 310 may be considered to be a component of the ultrasound transducer 316. For example, the transmitter 311, the receiver 318, and/or the beamforming electronics 320 may each be a component of the ultrasound transducer 316. In some embodiments, two or more components of the ultrasound system 310 are integrated into an integrated circuit, which may be a component of the ultrasound transducer 316. For example, the transmitter 312, the receiver 318, and/or the beamforming electronics 320 may be integrated into an integrated circuit.

The ultrasound system 310 may include an ultrasound probe 334 that holds one or more various components of the ultrasound transducer 316. For example, as shown in FIG. 5, the ultrasound probe 334 holds the array of acoustic elements 312. In addition to the acoustic elements 312, and for example, the ultrasound probe 334 may hold the transmitter 311, the receiver 318, the beamforming electronics 320, and/or one or more integrated circuits that include any of the components 311, 318, and/or 320.

Figure 6:
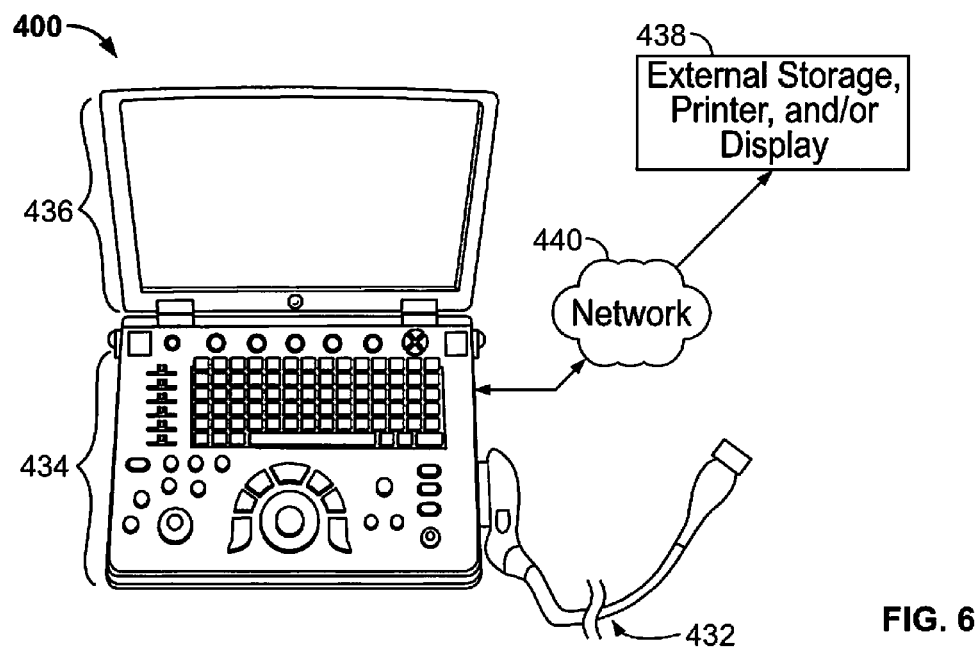
FIG. 6 is a diagram illustrating a three-dimensional (3D) capable miniaturized ultrasound system in which various embodiments may be implemented.
Figure 7:
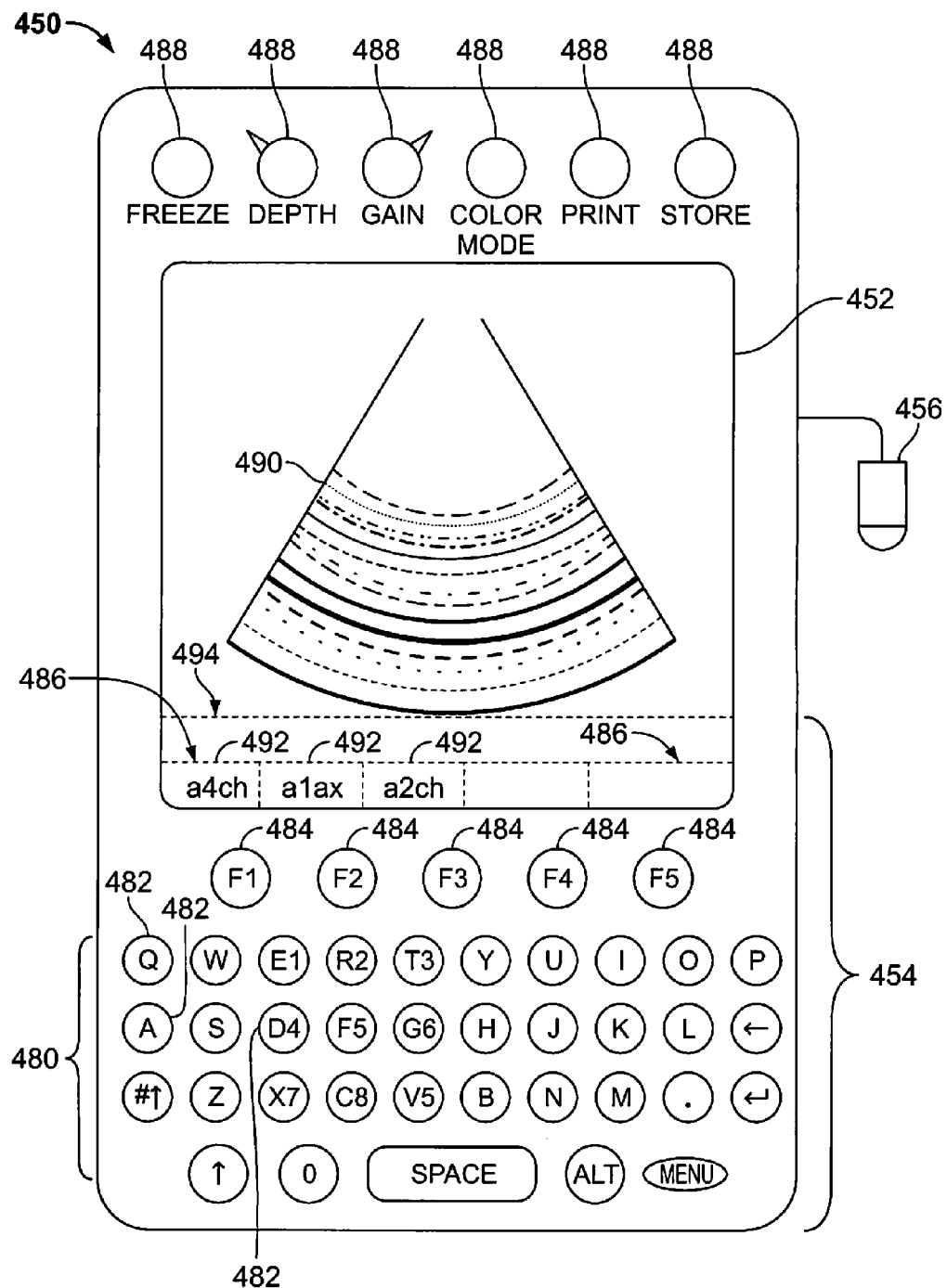
FIG. 7 is a diagram illustrating a 3D capable hand carried or pocket-sized ultrasound imaging system in which various embodiments may be implemented.
Figure 8:
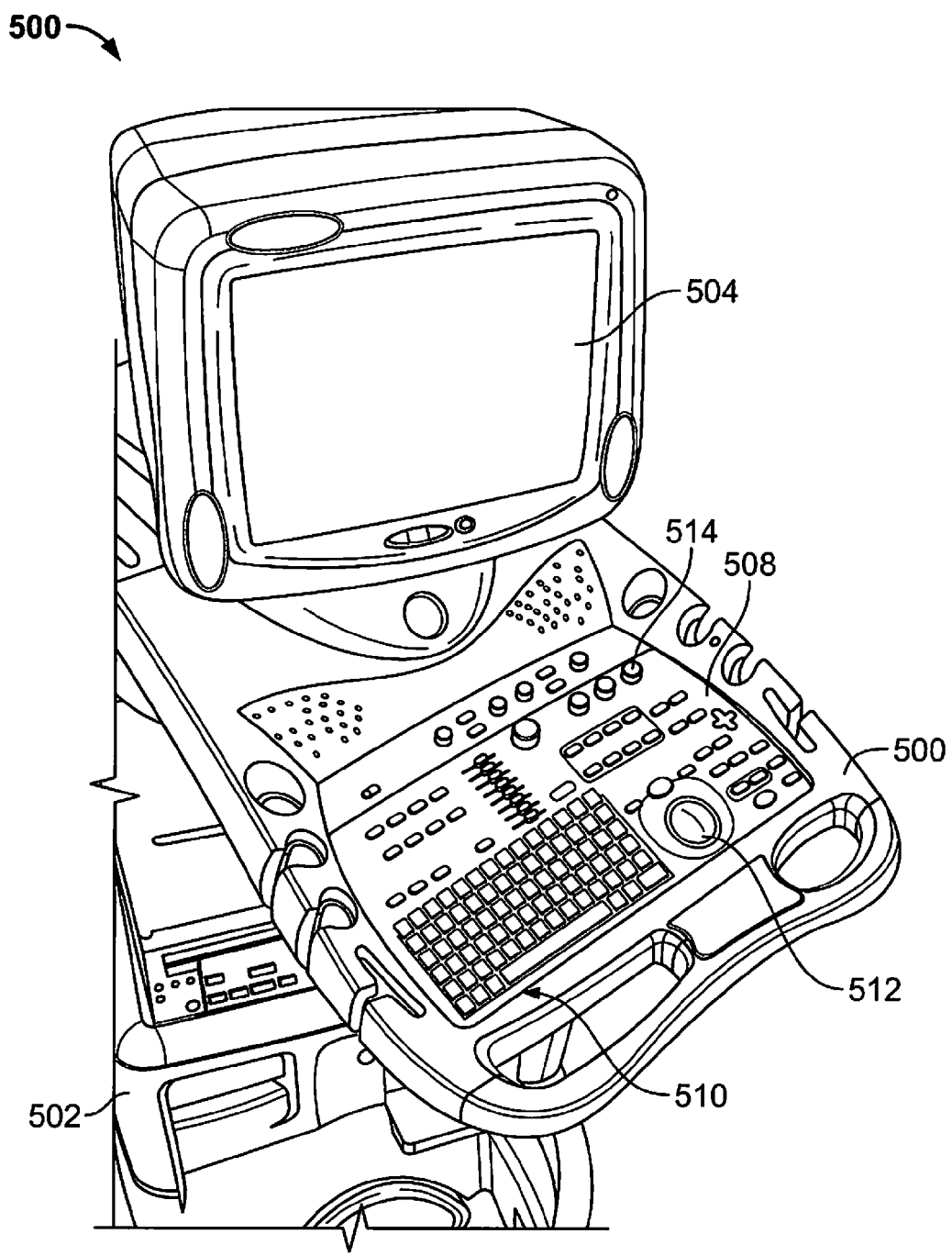
FIG. 8 is a diagram illustrating a 3D capable console type ultrasound imaging system in which various embodiments may be implemented.

The ultrasound system 310 may be embodied in a small-sized system, such as, but not limited to, a laptop computer or pocket sized system as well as in a larger console-type system. FIGS. 6 and 7 illustrate small-sized systems, while FIG. 8 illustrates a larger system.

FIG. 6 illustrates a 3D-capable miniaturized ultrasound system 400 having an ultrasound transducer 432 that may be configured to acquire 3D ultrasonic data or multi-plane ultrasonic data. For example, the ultrasound transducer 432 may have a 2D array of acoustic elements. A user interface 434 (that may also include an integrated display 436) is provided to receive commands from an operator. As used herein, "miniaturized" means that the ultrasound system 430 is a handheld or hand-carried device or is configured to be carried in a person's hand, pocket, briefcase-sized case, or backpack. For example, the ultrasound system 430 may be a hand-carried device having a size of a typical laptop computer. The ultrasound system 430 is easily portable by the operator. The integrated display 436 (e.g., an internal display) is configured to display, for example, one or more medical images.

The ultrasonic data may be sent to an external device 438 via a wired or wireless network 440 (or direct connection, for example, via a serial or parallel cable or USB port). In some embodiments, the external device 438 may be a computer or a workstation having a display, or the DVR of the various embodiments. Alternatively, the external device 438 may be a separate external display or a printer capable of receiving image data from the hand carried ultrasound system 430 and of displaying or printing images that may have greater resolution than the integrated display 436.

FIG. 7 illustrates a hand carried or pocket-sized ultrasound imaging system 450 wherein the display 452 and user interface 454 form a single unit. By way of example, the pocket-sized ultrasound imaging system 450 may be a pocket-sized or hand-sized ultrasound system approximately 2 inches wide, approximately 4 inches in length, and approximately 0.5 inches in depth and weighs less than 3 ounces. The pocket-sized ultrasound imaging system 450 generally includes the display 452, user interface 454, which may or may not include a keyboard-type interface and an input/output (I/O) port for connection to a scanning device, for example, and an ultrasound transducer 456. The display 452 may be, for example, a 320×320 pixel color LCD display (on which a medical image 484 may be displayed). A typewriter-like keyboard 480 of buttons 482 may optionally be included in the user interface 454.

Multi-function controls 484 may each be assigned functions in accordance with the mode of system operation (e.g., displaying different views). Therefore, each of the multi-function controls 484 may be configured to provide a plurality of different actions. Label display areas 486 associated with the multi-function controls 484 may be included as necessary on the display 452. The system 450 may also have additional keys and/or controls 488 for special purpose functions, which may include, but are not limited to "freeze," "depth control," "gain control," "color-mode," "print," and "store."

One or more of the label display areas 486 may include labels 492 to indicate the view being displayed or allow a user to select a different view of the imaged object to display. The selection of different views also may be provided through the associated multi-function control 484. The display 452 may also have a textual display area 494 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 450 and the miniaturized ultrasound system 400 may provide the same scanning and processing functionality as the system 310 (shown in FIG. 5)

FIG. 8 illustrates an ultrasound imaging system 500 provided on a movable base 502. The portable ultrasound imaging system 500 may also be referred to as a cart-based system. A display 504 and user interface 506 are provided and it should be understood that the display 504 may be separate or separable from the user interface 506. The user interface 506 may optionally be a touchscreen, allowing the operator to select options by touching displayed graphics, icons, and/or the like.

The user interface 506 also includes control buttons 508 that may be used to control the portable ultrasound imaging system 500 as desired or needed, and/or as typically provided. The user interface 506 provides multiple interface options that the user may physically manipulate to interact with ultrasound data and other data that may be displayed, as well as to input information and set and change scanning parameters and viewing angles, etc. For example, a keyboard 510, trackball 512 and/or multi-function controls 514 may be provided.

It should be noted that although the various embodiments may be described in connection with an ultrasound system, the methods and systems are not limited to ultrasound imaging or a particular configuration thereof. The various embodiments of ultrasound imaging may be implemented in combination with different types of imaging systems, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An ultrasound transducer comprising:
    an acoustic layer having a front side and an opposite back side, the acoustic layer being configured to convert electrical signals into ultrasound waves to be transmitted from the front side toward a target, the acoustic layer being configured to convert received ultrasound waves into electrical signals;
    a lens connected to the front side of the acoustic layer;
    a heat sink connected to the back side of the acoustic layer; and
    a flex circuit disposed between the acoustic layer and the heat sink, the flex circuit comprising a backside matching layer incorporated into a body of the flex circuit, wherein the backside matching layer is connected in thermal communication with the acoustic layer and the heat sink such that the backside matching layer is configured to conduct heat from the acoustic layer to the heat sink.

2. The ultrasound transducer of claim 1, wherein the backside matching layer is an interior layer of the body of the flex circuit.

3. The ultrasound transducer of claim 1, wherein the backside matching layer is an exterior layer of the body of the flex circuit.

4. The ultrasound transducer of claim 1, wherein the body of the flexible circuit comprises first and second dielectric coverlaps and an electrical signal layer disposed between the first and second dielectric coverlaps, the backside matching layer being disposed within the body of the flexible circuit between the electrical signal layer and the second dielectric coverlap.

5. The ultrasound transducer of claim 1, wherein the body of the flex circuit comprises an exterior acoustic layer side and an opposite exterior heat sink side, the acoustic layer side facing the acoustic layer, the heat sink side facing the heat sink, the backside matching layer defining the heat sink side of the body of the flex circuit.

6. The ultrasound transducer of claim 1, wherein the body of the flexible circuit comprises first and second dielectric coverlaps, an electrical signal layer, and an interior dielectric layer, the electrical signal layer being disposed between the first dielectric coverlap and the interior dielectric layer, the interior dielectric layer being disposed between the electrical signal layer and the backside matching layer, the backside matching layer being disposed between the interior dielectric layer and the second dielectric coverlap.

7. The ultrasound transducer of claim 1, wherein the body of the flex circuit comprises first and second dielectric coverlaps and an electrical signal layer disposed between the first and second dielectric coverlaps, the first dielectric coverlap extending between the electrical signal layer and the acoustic layer, the second dielectric coverlap extending between the electrical signal layer and the heat sink, the backside matching layer being laminated to the second dielectric coverlap of the body of the flex circuit such that the backside matching layer extends between the second dielectric coverlap and the heat sink.

8. The ultrasound transducer of claim 1, wherein the backside matching layer comprises a wing that extends beyond an end of the acoustic layer and is engaged in physical contact with the heat sink.

9. The ultrasound transducer of claim 1, further comprising a thermally conductive sheet that is engaged in physical contact with both the backside matching layer and the heat sink for conducting heat from the backside matching layer to the heat sink.

10. The ultrasound transducer of claim 1, wherein the lens is indirectly connected to the front side of the acoustic layer through one or more frontside matching layers disposed between the acoustic layer and the lens.

11. The ultrasound transducer of claim 1, wherein the flex circuit is indirectly connected to the back side of the acoustic layer through one or more dematching layers disposed between the acoustic layer and the flex circuit.

12. The ultrasound transducer of claim 1, further comprising a thermal backing disposed between the flex circuit and the heat sink, wherein the thermal backing has a thermal conductivity of less than approximately 10 W/mK.

13. A method for manufacturing an ultrasound transducer, the method comprising:
    providing a completed flex circuit that includes a backside matching layer incorporated into a body of the flex circuit; and
    assembling the ultrasound transducer using the completed flex circuit, wherein assembling the ultrasound transducer comprises:
        connecting a lens to a front side of an acoustic layer;
        connecting the flex circuit to a back side of the acoustic layer; and
        connecting a heat sink to the flex circuit such that the backside matching layer of the flex circuit is connected in thermal communication between the back side of the acoustic layer and the heat sink for conducting heat from the acoustic layer to the heat sink.

14. The method of claim 13, wherein providing the completed flex circuit comprises receiving the completed flex circuit from a supplier of the flex circuit.

15. The method of claim 13, wherein providing the completed flex circuit comprises providing the flex circuit with the backside matching layer as an interior layer of the body of the flex circuit.

16. The method of claim 13, wherein providing the completed flex circuit comprises providing the flex circuit with the backside matching layer as an exterior layer of the body of the flex circuit.

17. The method of claim 13, wherein connecting the lens to the front side of the acoustic layer comprises indirectly connecting the lens to the front side of the acoustic layer using one or more frontside matching layers disposed between the acoustic layer and the lens.

18. The method of claim 13, wherein connecting the flex circuit to the back side of the acoustic layer comprises indirectly connecting the flex circuit to the back side of the acoustic layer using one or more dematching layers disposed between the acoustic layer and the flex circuit.

19. An ultrasound transducer comprising:
    an acoustic layer having a front side and an opposite back side, the acoustic layer being configured to convert electrical signals into ultrasound waves to be transmitted from the front side toward a target, the acoustic layer being configured to convert received ultrasound waves into electrical signals;
    a lens connected to the front side of the acoustic layer;
    a heat sink connected to the back side of the acoustic layer; and
    a flex circuit disposed between the acoustic layer and the heat sink, the flex circuit having a body comprising first and second dielectric coverlaps and an electrical signal layer disposed between the first and second dielectric coverlaps, the body further comprising a backside matching layer disposed within the body between the electrical signal layer and the second dielectric coverlap, wherein the backside matching layer is connected in thermal communication with the acoustic layer and the heat sink such that the backside matching layer is configured to conduct heat from the acoustic layer to the heat sink.

20. The ultrasound transducer of claim 19, wherein the body of the flexible circuit comprises an interior dielectric layer, the electrical signal layer being disposed between the first dielectric coverlap and the interior dielectric layer, the interior dielectric layer being disposed between the electrical signal layer and the backside matching layer, the backside matching layer being disposed between the interior dielectric layer and the second dielectric coverlap.

* * * * *